US009566215B2

(12) United States Patent
Fukuoka

(10) Patent No.: US 9,566,215 B2
(45) Date of Patent: Feb. 14, 2017

(54) DRUG DELIVERY DEVICE

(75) Inventor: Koji Fukuoka, Kobe (JP)

(73) Assignee: KOBAYASHI & CO., LTD., Tokyo (JP)

( * ) Notice: Subject to any disclaimer, the term of this patent is extended or adjusted under 35 U.S.C. 154(b) by 358 days.

(21) Appl. No.: 14/389,637

(22) PCT Filed: Apr. 2, 2012

(86) PCT No.: PCT/JP2012/058844
§ 371 (c)(1),
(2), (4) Date: Sep. 30, 2014

(87) PCT Pub. No.: WO2013/150579
PCT Pub. Date: Oct. 10, 2013

(65) Prior Publication Data
US 2015/0209233 A1 Jul. 30, 2015

(51) Int. Cl.
*A61B 19/00* (2006.01)
*A61J 1/20* (2006.01)

(52) U.S. Cl.
CPC ............. *A61J 1/2096* (2013.01); *A61J 1/2048* (2015.05); *A61J 1/201* (2015.05); *A61J 1/2013* (2015.05); *A61J 1/2051* (2015.05); *A61J 1/2058* (2015.05); *A61J 1/2086* (2015.05)

(58) Field of Classification Search
CPC ...... A61J 1/2096; A61J 1/2013; A61J 1/2086; A61J 1/2048; A61J 1/2055
See application file for complete search history.

(56) References Cited

U.S. PATENT DOCUMENTS

| | | | |
|---|---|---|---|
| 5,122,123 | A | 6/1992 | Vaillancourt |
| 5,832,971 | A | 11/1998 | Yale et al. |
| 2009/0216212 | A1 | 8/2009 | Fangrow, Jr. |
| 2012/0172830 | A1 | 7/2012 | Yokoyama et al. |

FOREIGN PATENT DOCUMENTS

| | | | |
|---|---|---|---|
| JP | 53-115589 | | 10/1978 |
| JP | 60-154858 | U | 10/1985 |
| JP | 5-200098 | A | 8/1993 |
| JP | 8-71121 | A | 3/1996 |

(Continued)

OTHER PUBLICATIONS

International Search Report dated Jun. 12, 2012 issued in corresponding application No. PCT/JP2012/058844.

*Primary Examiner* — Leslie Deak
(74) *Attorney, Agent, or Firm* — Westerman, Hattori, Daniels & Adrian, LLP

(57) ABSTRACT

This drug delivery device delivers a drug between a syringe barrel and a drug container, and, by enveloping the entire the drug container used in drug delivery, prevents exposure to hazardous drugs adhering to the drug container. This drug delivery device includes: a first member connected to the drug container on the side of a stopper; a second member connected to the first member and to the syringe barrel; and a third member connected to the first member and covering the drug container in a sealed state. The first member has a first hollow needle member and a drug container holder, and the second member has a second hollow needle member. The third member has an opening portion, a bottom surface portion where the drug container is stably mounted, and a flexible member which is connected to the opening portion and the bottom surface portion.

3 Claims, 12 Drawing Sheets

(56) References Cited

FOREIGN PATENT DOCUMENTS

| | | | |
|---|---|---|---|
| JP | 10-295780 | A | 11/1998 |
| JP | 2010-521219 | A | 6/2010 |
| JP | 2010-525920 | A | 7/2010 |
| JP | 2010-528808 | A | 8/2010 |
| JP | 2010-528809 | A | 8/2010 |
| JP | 2010-528810 | A | 8/2010 |
| JP | 2010-537900 | A | 12/2010 |
| JP | 2011-512205 | A | 4/2011 |
| WO | 2008/115102 | A1 | 9/2008 |
| WO | 2008/136720 | A1 | 11/2008 |
| WO | 2008/153458 | A1 | 12/2008 |
| WO | 2008/153459 | A1 | 12/2008 |
| WO | 2008/153460 | A1 | 12/2008 |
| WO | 2009/029010 | A1 | 3/2009 |
| WO | 2011/030787 | A1 | 3/2011 |

(a)

(b)

DRUG DELIVERY DEVICE

TECHNICAL FIELD

The present invention relates to technology pertaining to devices for causing delivery of drug(s) between or among syringe barrels) and/or drug container(s).

BACKGROUND ART

Among the anticancer agents and other such hazardous medications which are used in medical facilities there are a wide variety of products which include therapeutic radioactive medications and the like. Hazardous medications are drugs which are used on a daily basis consistent with therapeutic objectives at medical facilities. However, as levels of mutagens detected in the urine of medical staff who work in environments where these are formulated or administered are high as compared with medical staff who have not been exposed thereto, there is concern that there may be adverse effect on reproductive function.

The U.S. Occupational Safety and Health Administration has published guidelines related to the handling of antineoplastic agents and other hazardous medications by medical staff, and regulations for the handling of hazardous medications have also been established at institutions such as the U.S. National Institutes of Health (NIH). However, during handling of hazardous medications at medical facilities, there are still many situations in which medical staff and patients are subjected to unintentional exposure by those hazardous medications. In such situations, it is frequently the case that the route by which exposure occurs is oral or transdermal exposure to the hazardous medication in liquid or gas form.

More specifically, exposure frequently occurs as a result of drug leakage or dripping at times such as when an infusion bag is being filled with a drug or when a drug is being transferred by suction from a drug container to a syringe during drug dispensing operations. Even more specifically, it is believed that following leakage the drug may come in direct contact with the skin, or that the drug in gasified form, or in particulate form and floating in the air where the drug has dried, may enter the body by inhalation.

In light of the foregoing situation, many medical devices have been developed for delivery of drug(s) between or among containers in which, where hazardous drugs are to be delivered between or among containers, employment of a closed system between or among those containers has been attempted in an effort to prevent medical staff and patients from being subjected to exposure by hazardous drugs (see Patent References Nos. 1 through 6).

PRIOR ART REFERENCES

Patent References

Patent Reference No. 1: Japanese Patent Application Publication Kokai No. 2010-521219

Patent Reference No. 2: Japanese Patent Application Publication Kokai No. 2010-525920

Patent Reference No. 3: Japanese Patent Application Publication Kokai No. 2010-528808

Patent Reference No. 4: Japanese Patent Application Publication Kokai No. 2010-528809

Patent Reference No. 5: Japanese Patent Application Publication Kokai No. 2010-528810

Patent Reference No. 6: Japanese Patent Application Publication Kokai No. 2010-537900

SUMMARY OF INVENTION

Problem to be Solved by Invention

However, there is a problem in the conventional art in that exposure to hazardous drugs adhering to the drug containers cannot be prevented.

The present invention therefore proposes a drug delivery device that delivers drug(s) between syringe barrel(s) and drug container(s), and that, by enveloping the entire container(s) at drug container(s) employed for delivery of drug(s), prevents exposure to hazardous drug(s) adhering to drug container(s).

Means for Solving Problem

One embodiment of a drug delivery device that is disclosed is a drug delivery device that has a first member which is connected to a stopper side of a drug delivery device, a second member which is connected at one end thereof to said first member and which is connected at another end thereof to a syringe barrel, and a third device which is connected to the first member and which is for covering the drug container in a sealed state; that carries out delivery of a drug between the drug container and the syringe barrel; and that is characterized in that: the first member has a first hollow needle member having a tip portion arranged so as to be directed toward the stopper side of the drug delivery device, and having a base portion arranged so as to be directed toward the second member, the base portion and the tip portion each being provided with a hole for delivery of the drug; and a drug container gripping portion that allows a size of a region at which connection occurs to be varied in correspondence to a magnitude of an outside diameter at the drug container stopper portion, and that squeezes on and holds the drug container stopper; the second member has a second hollow needle member having a tip portion arranged so as to be directed toward the first member, and having a base portion arranged so as to be directed toward the syringe barrel, the base portion and the tip portion each being provided with a hole for delivery of the drug; and the third member has an open portion; a bottom portion permitting stable placement of the drug container thereon; and a flexible member that is connected at one end thereof to the open portion and is connected at another end thereof to the bottom portion, that allows the drug container when placed on the bottom portion to be visible from an exterior side, that is of adjustable height, and that covers the drug container; wherein mounting the open portion on the first member while in a state in which the flexible member covers the drug container gripping portion causes the first member and the third member to be mutually connected while an interior of the third member is in a sealed state; wherein, when the first member and the second member are mutually connected, the second hollow needle member is inserted within the first hollow needle member which is inserted in the stopper of the drug container; and wherein, after the drug container gripping portion has caused the connected relationship between the drug container and the first member to become fixed, delivery of the drug between the drug container and the syringe barrel is carried out by way of the first hollow needle member and the second hollow needle member which is inserted within said first hollow needle member.

Furthermore, one embodiment of a drug delivery device that is disclosed is characterized in that, in addition to the foregoing constitution, the bottom portion has a magnifying lens capable of magnifying and making visible a drug container bottom placed on the bottom portion.

Furthermore, one embodiment of a drug delivery device that is disclosed is characterized in that, in addition to the foregoing constitution, a size of the open portion is adjustable.

Benefit of the Invention

A drug delivery device which is disclosed, by enveloping the entire container(s) at drug container(s) employed for delivery of drug(s), permits delivery of drug(s) between syringe barrel(s) and drug container(s) while preventing exposure to hazardous drug(s) adhering to drug container(s).

EMBODIMENTS FOR CARRYING OUT THE INVENTION

Embodiments for carrying out the present invention will be described with reference to the drawings.

(Structure of Drug Delivery Device Associated with Present Embodiment)

Figure 1:
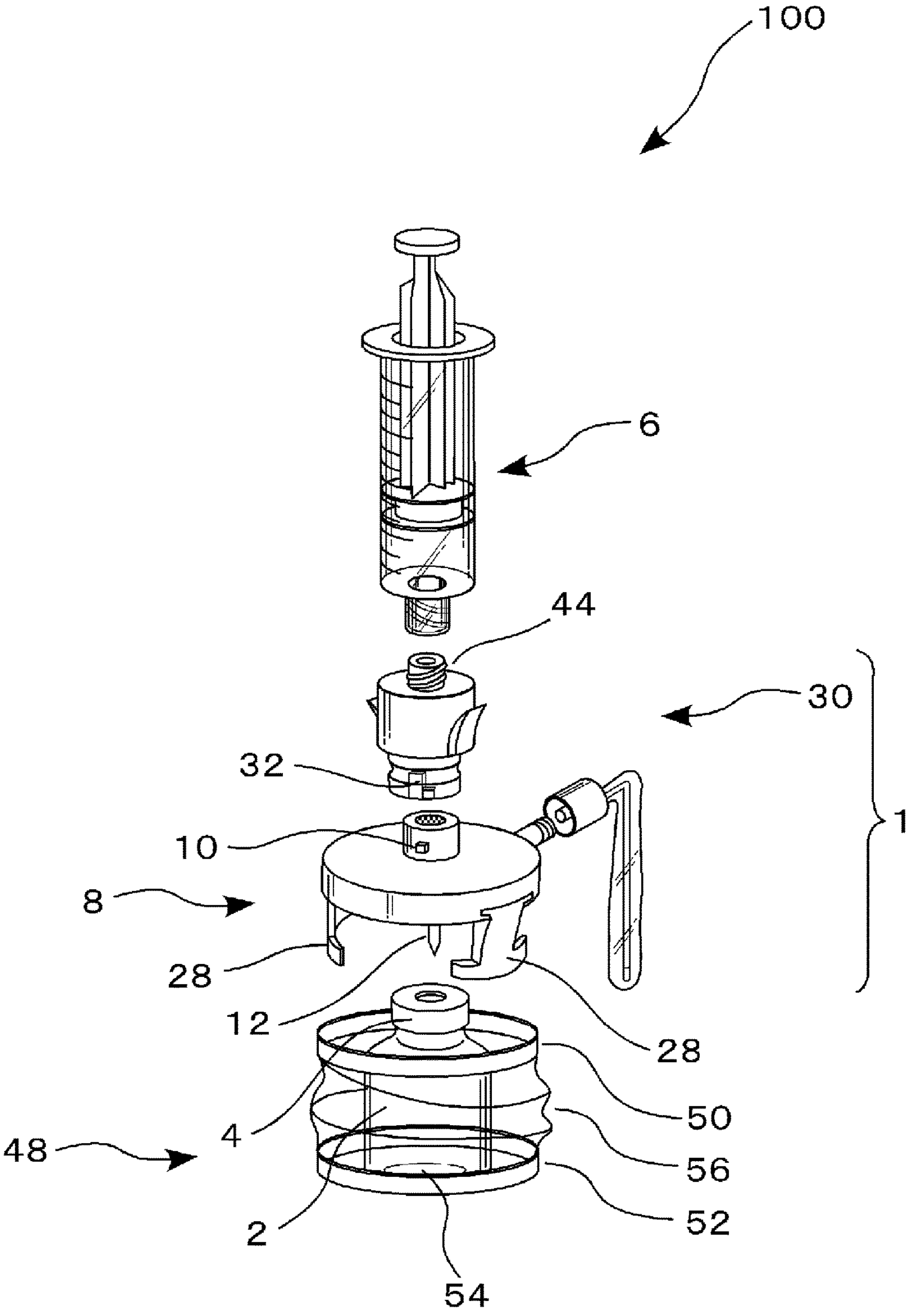
FIG. 1 Drawing showing an example of a drug delivery system which includes a drug delivery device associated with the present embodiment.

Structure of a drug delivery device 1 associated with the present embodiment will be described using FIG. 1 through FIG. 12. FIG. 1 is a drawing showing an overview of a drug delivery system 100 including drug delivery device(s) 1. As shown in FIG. 1, drug delivery system 100 has drug container(s) 2, syringe barrel(s) 6, first member(s) 8, second member(s) 30, and third member(s) 48.

Drug delivery system 100 uses first member(s) 8 and second member(s) 30 to cause connection between or among drug container(s) 2 and syringe barrel(s) 6, and with these in this connected state, to cause drug(s) in liquid and/or gas form to be delivered between drug container(s) 2 and syringe barrel(s) 6.

Moreover, at drug delivery system 100, as a result of causing mutual connection to be made between first member(s) 8 and third member(s) 48, in the interior(s) of which drug container(s) 2 are placed, delivery of drug(s) between drug container(s) 2 and syringe barrel(s) 6 is carried out in such fashion that drug container(s) 2 are isolated from the exterior.

Figure 2:
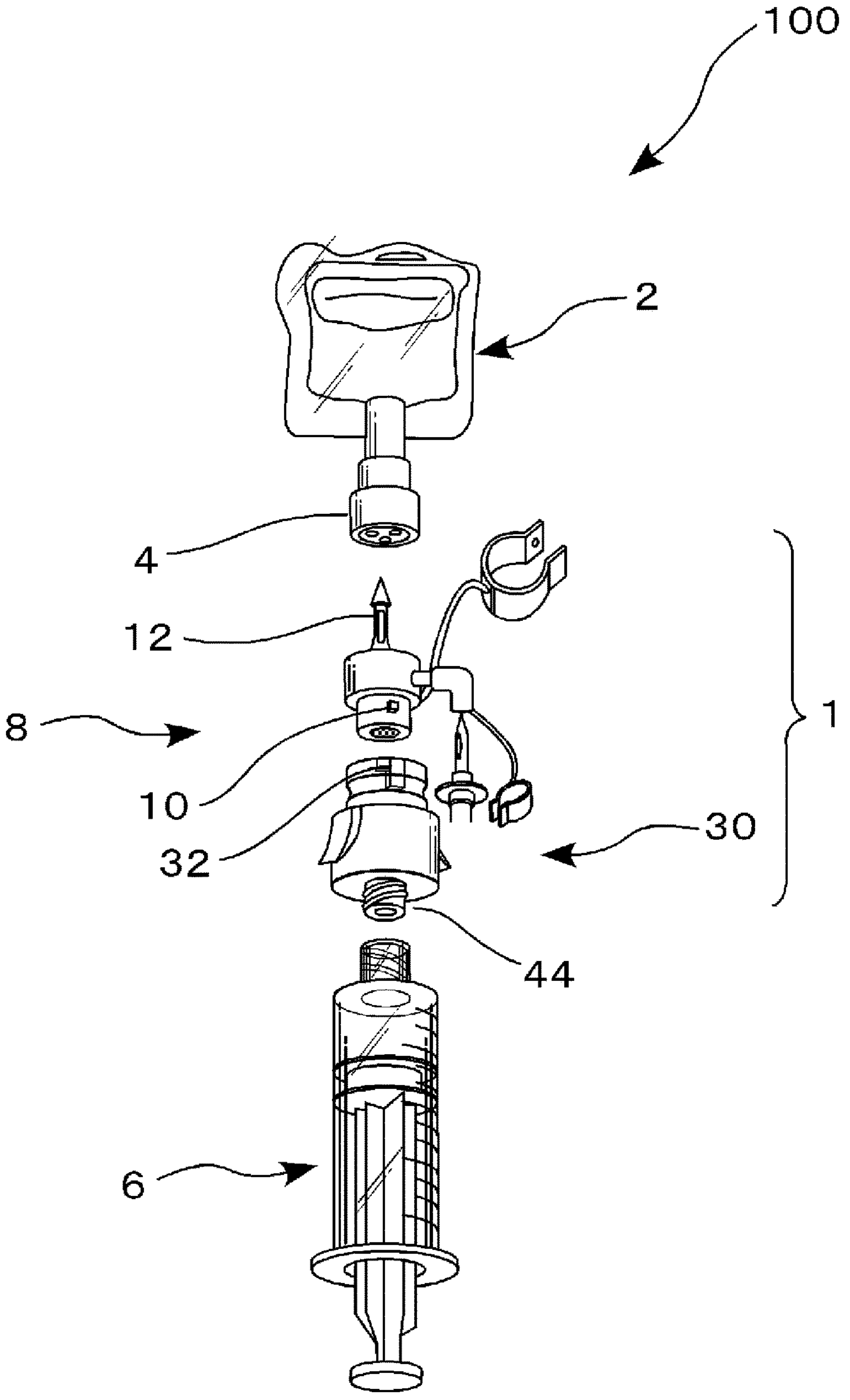
FIG. 2 Drawing showing an example of a drug delivery system which includes a drug delivery device associated with the present embodiment.
Figure 3:
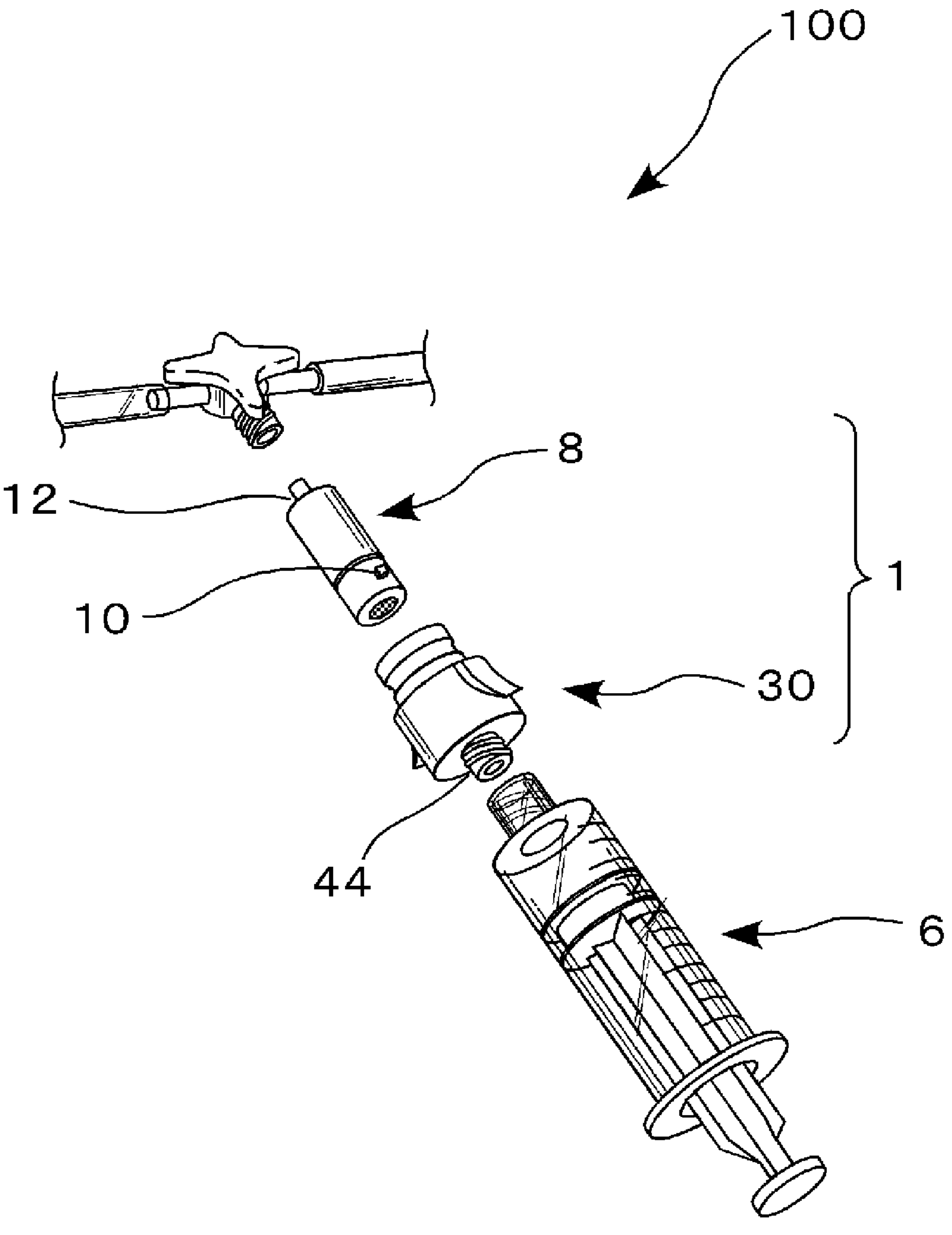
FIG. 3 Drawing showing an example of a drug delivery system which includes a drug delivery device associated with the present embodiment.

While it is preferred that drug container 2 be a vial (Vial) as shown in FIG. 1, it may also be an infusion bag as shown in FIG. 2; drug(s) in solid, liquid, and/or gas form are stored within the interior of drug container 2. As shown in FIG. 3, drug delivery device 1 is capable of being applied to a situation in which drug container 2 takes the form of an infusion line. Furthermore, drug container 2 is equipped with stopper(s) 4 which make connection(s) with other member(s) and which are used during delivery of drug(s). Drug container 2 is connected to first member(s) 8 on the side(s) thereof at which stopper(s) 4 is/are present.

Syringe barrel 6, also referred to as syringe (Syringe), is an apparatus for causing infusion and/or suction of drug(s) in liquid and/or gas form, and is not equipped with an injection needle. Syringe barrel 6 is connected to second member 30 at syringe barrel connection portion 44 provided on second member 30.

Furthermore, as shown in FIG. 1, first member 8 and second member 30 are mutually connected, and first member 8 and third member 48 are mutually connected.

Figure 4:
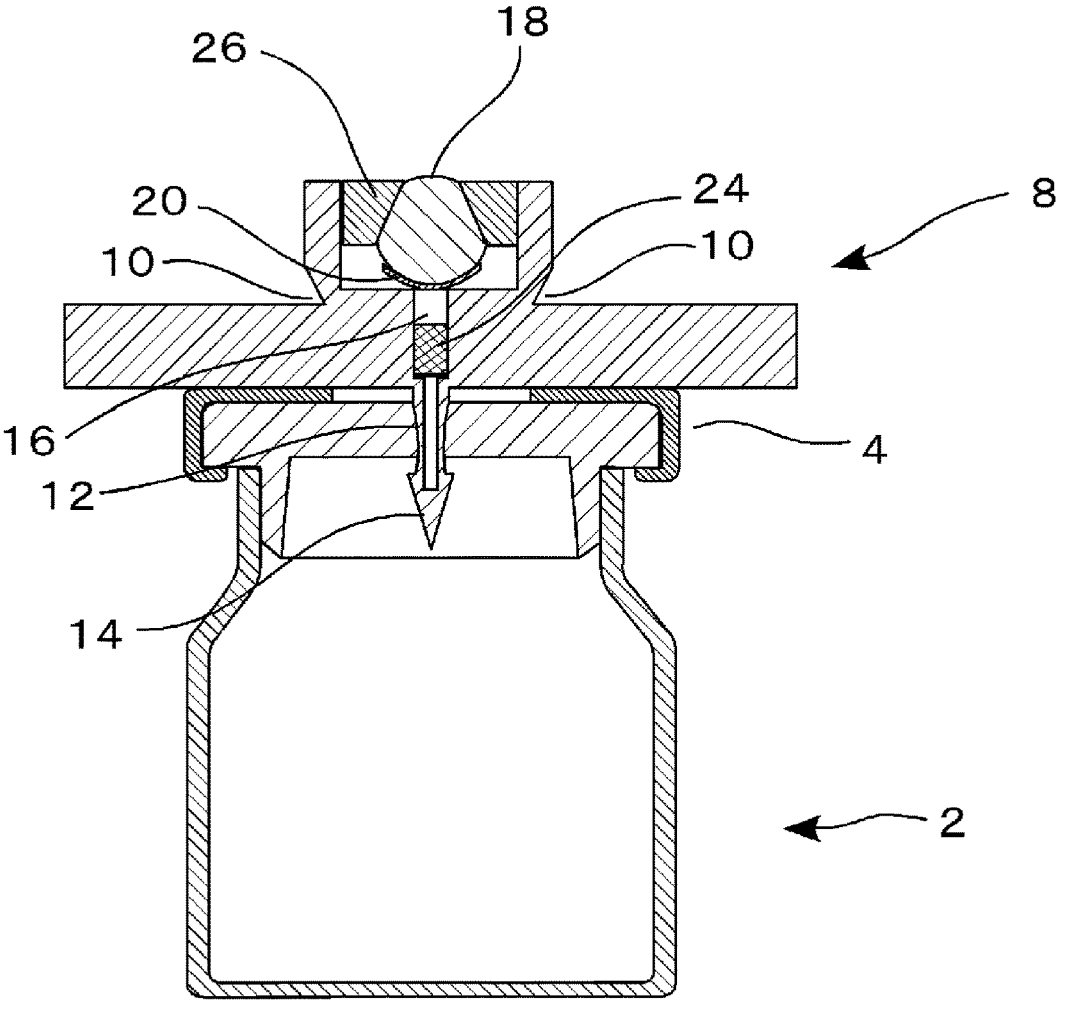
FIG. 4 Sectional view to assist in describing principal parts of a first member associated with the present embodiment.

Description of first member 8 will now be carried out using FIG. 4. FIG. 4 is a sectional view to assist in describing the principal parts of first member 8. As shown in FIG. 4, first member 8 has engagement mechanism male portion(s) 10, first hollow needle member(s) 12, first elastic member(s) 18, first fixing member(s) 26, first filter member(s) 20, second filter member(s) 24, and drug container gripping portion(s) 28.

Engagement mechanism male portion 10, which is the male portion of an engagement mechanism (locking mechanism) for causing mutual connection between first member 8 and second member 30, causes first member 8 and second member 30 to be mutually connected by means of a simple operation as a result of engagement with female portion 32 provided on second member 30, described below. This engagement mechanism might for example be a mechanism comprising a pawl-shaped female portion and a male portion shaped so as to engage with this pawl, first member 8 and second member 30 being capable of being easily locked in connected relationship as a result of the mutual engagement which is made to occur between this pawl and this region that engages with the pawl. Note that the foregoing engagement mechanism may have a structure which is other than this.

First hollow needle member 12, which is needle-shaped and has hollow interior, is such that tip portion 14 thereof is arranged so as to be directed toward stopper 4 of drug container 2, and is such that base portion 16 thereof is arranged so as to be directed toward the portion which makes connection with second member 30. Furthermore, liquid drug delivery between drug container 2 and syringe barrel 6 is carried out while in a state in which tip portion 14 is inserted within stopper 4 of drug container 2. For this reason, hole(s) for delivery of drug(s) are provided at least at tip portion 14 and base portion 16.

First elastic member 18 might for example be a spherically shaped member, the material of which is silicon, thermoplastic resin, or other such substance provided with elasticity. Furthermore, first elastic member 18 is held in fixed fashion at a prescribed location within first member 8 by first fixing member 26. Here, what is meant by a prescribed location is a location at which first elastic member 18 occludes hole(s) in base portion 16 of first hollow needle member 12.

First fixing member 26, as has been described, is a member for holding first elastic member 18 in fixed fashion at a prescribed location within first member 8. First fixing member 26 is of bowl-like shape and has hole(s) at the base portion thereof, engagement of this bowl-like region by the spherically shaped first elastic member 18 causing first elastic member 18 to be held in fixed fashion at the prescribed location.

First filter member 20 is a member which acts to prevent debris (hereinafter also referred to as "unwanted material") 46 from elastic members 18, 40, generated by second hollow needle member 34 when—as will be described below—it penetrates elastic members 18, 40 and is inserted within first hollow needle member 12, from being able to enter the interior of first hollow needle member 12. First filter member 20 is arranged between hole(s) present in base portion 16 of first hollow needle member 12 and first elastic member 18.

Figure 5:
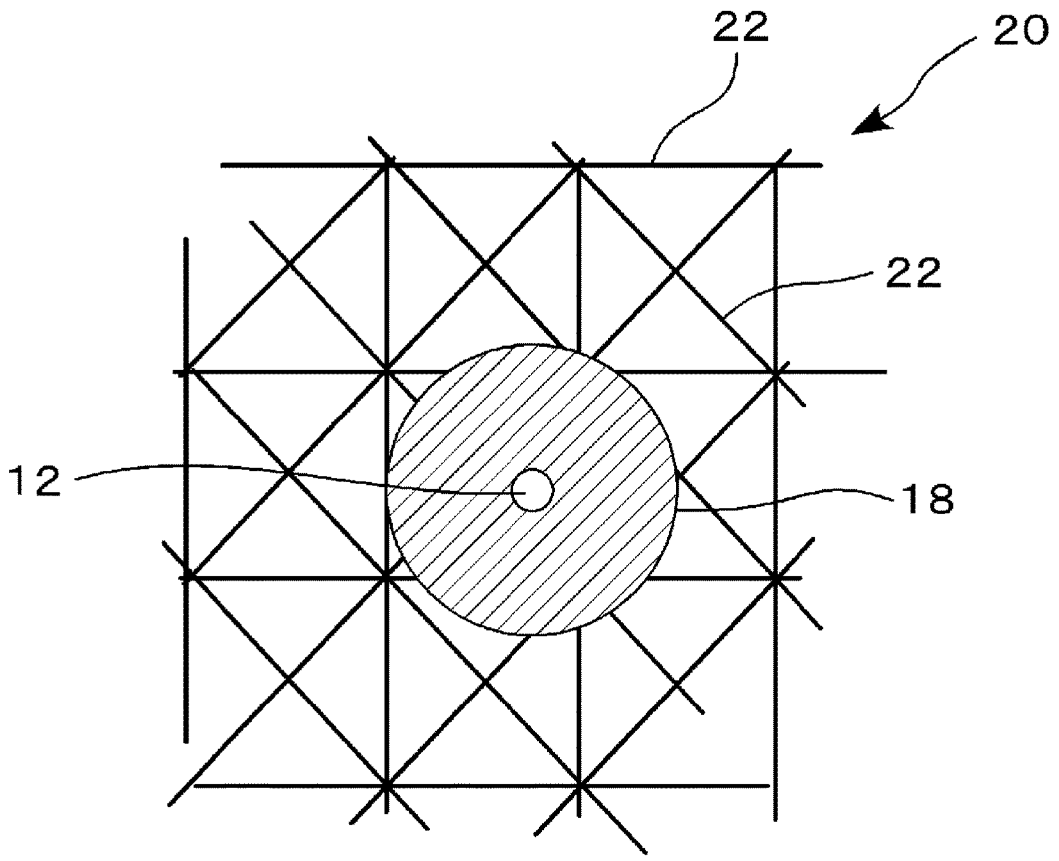
FIG. 5 Plan view to assist in describing principal parts of a first filter member associated with the present embodiment.

FIG. 5 is a drawing to assist in describing the structure of first filter member 20 at this time. As shown in FIG. 5, first filter member 20 is constituted such that there is a screen-like member 22 in which thread-like member(s) are arranged in screen-like (lattice-like) fashion, over which and rotated with respect to which by on the order of 45° there is a screen-like member 22. Note, however, that whereas first filter member 20 is a member which is installed for the purpose of preventing debris 46 which may be produced by scraping of elastic members 18, 40 due to action of second hollow needle member 34 from being able to enter the interior of first hollow needle member 12, so long as this purpose is achieved, it is not limited to the foregoing constitution.

Second filter member 24, like first filter member 20, is a member which acts to prevent unwanted material 46 generated by second hollow needle member 34 from being able to enter the interior of first hollow needle member 12 (particularly tip portion 14). Second filter member 24 is installed within the interior of first hollow needle member 12. There is no limitation with respect to the material or structure of second filter member 24 so long as the foregoing purpose is achieved.

Figure 6:
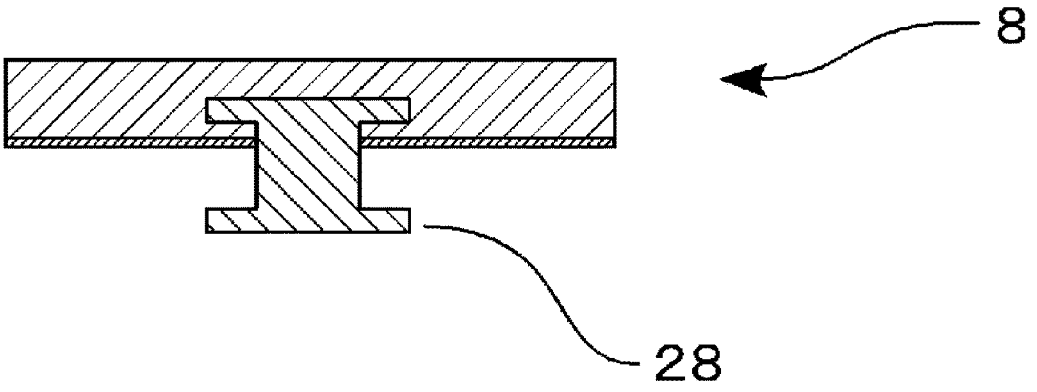
FIG. 6 Drawing to assist in describing principal parts of a drug container gripping portion associated with the present embodiment.
Figure 6:
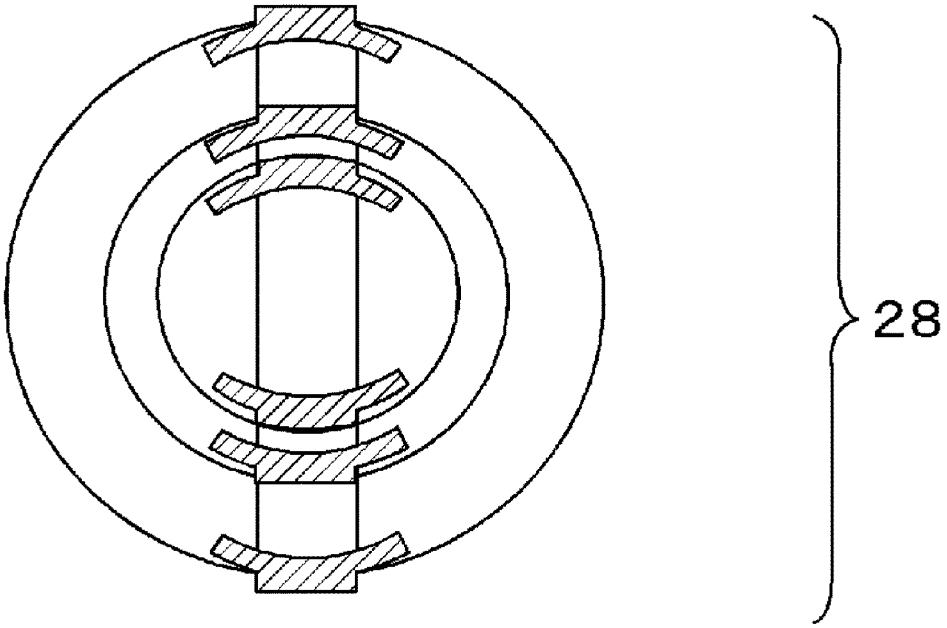
Figure 7:
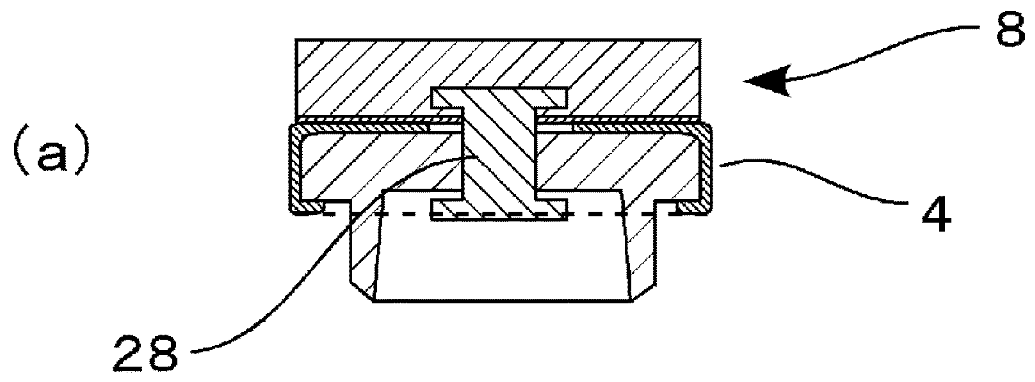
FIG. 7 Drawing to assist in describing examples of how a drug container gripping portion associated with the present embodiment may be applied in various situations.
Figure 7:
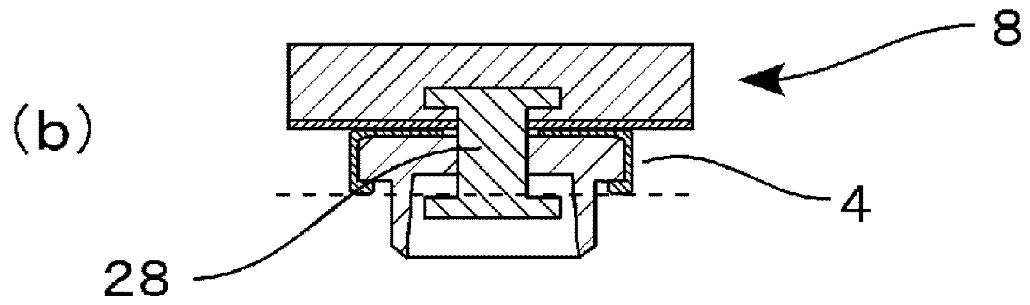
Figure 7:
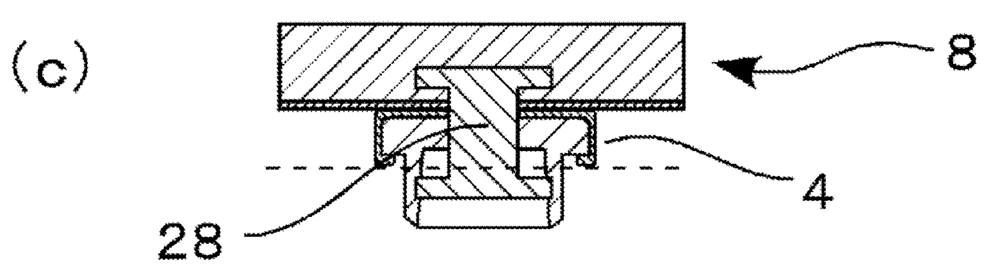

Next, FIG. 6 and FIG. 7 will be used to describe drug container gripping portion 28. FIG. 6(*a*) is a front view to assist in describing the principal parts of drug container gripping portion 28; FIG. 6(*b*) is a plan view to assist in describing the principal parts of drug container gripping portion 28. FIG. 7(*a*) through (*c*), are respectively drawings to assist in describing how the size of drug container gripping portion 28 might be varied so as to accommodate stoppers 4 of various size.

Stopper 4 of drug container 2 may be of various sizes, the diameter of the opening being 15 mm, 20 mm, 30 mm, or the like. Accordingly, as shown at FIG. 6(*a*), drug container gripping portion 28 is a member which, by squeezing on the stopper 4 and/or nose portion of drug container 2 from the side(s) thereof, causes the mutually connected relationship between drug container 2 and first member 8 to be made fixed. Furthermore, as shown at FIG. 6(*b*), drug container gripping portion 28 is such that size(s) of region(s) at which connection is made can be adjusted so as to be size(s) of stopper(s) 4 (and/or nose portion(s)) of drug container(s) 2.

In addition, as respectively shown at FIG. 7(*a*) through (*c*), drug container gripping portion 28 is such that the size of the region at which connection occurs is made to correspond to the size of stopper 4 (and/or the nose portion) of drug container 2, so that when stopper 4 (and/or the nose portion) is squeezed on from both the left and right sides thereof, and/or from all four sides thereof, this causes the mutually connected relationship between drug container 2 and first member 8 to be made fixed.

Figure 8:
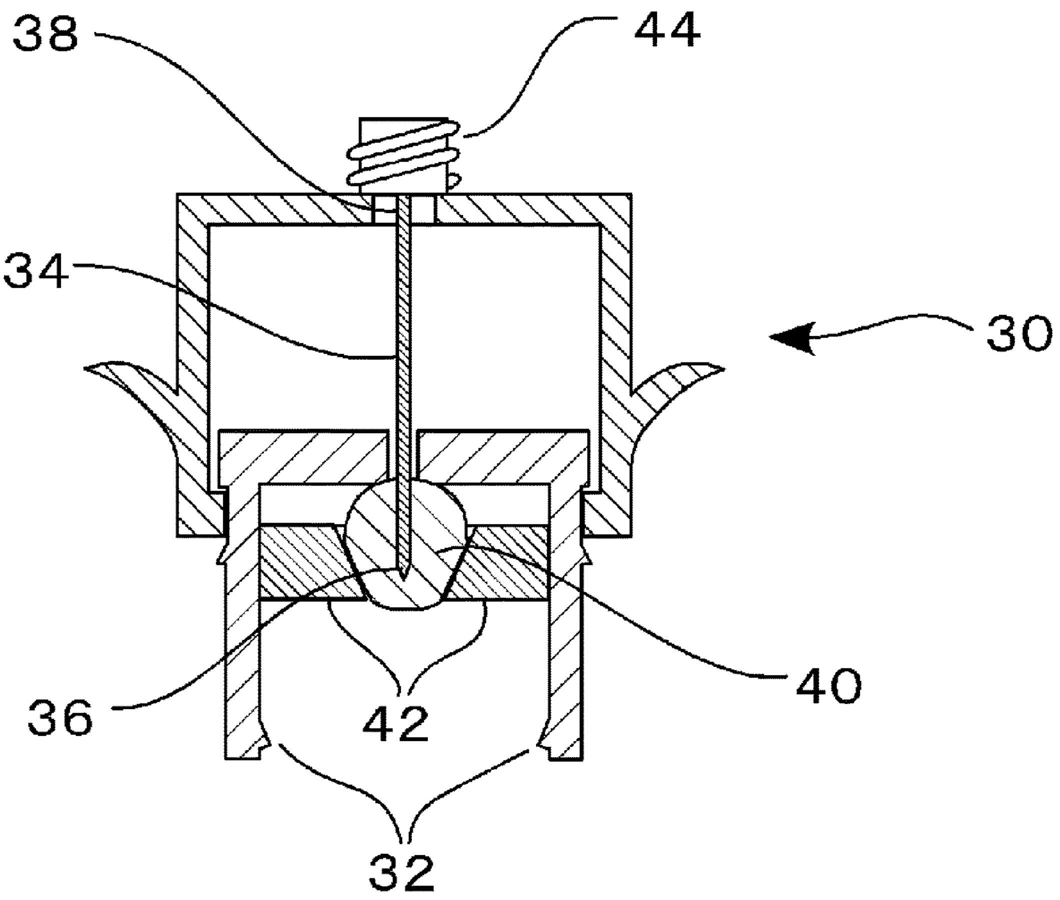
FIG. 8 Sectional view to assist in describing principal parts of a second member associated with the present embodiment.

Next, FIG. 8 will be used to describe second member 30. FIG. 8 is a sectional view to assist in describing the principal parts of second member 30. As shown in FIG. 8, second member 30 has syringe barrel connection portion(s) 44, engagement mechanism female portion(s) 32, second hollow needle member(s) 34, second elastic member(s) 40, and second fixing member(s) 42.

Syringe barrel connection portion 44, which is the region which makes connection with syringe barrel 6 into which the liquid or gas drug which is delivered will be deposited, is located at the end which is opposite the region that makes connection with first member 8. There is no particular limitation with respect to the mechanism by means of which syringe barrel connection portion 44 and syringe barrel 6 are mutually connected.

Engagement mechanism female portion 32, which is the female portion of an engagement mechanism (locking mechanism) for causing mutual connection between first member 8 and second member 30, causes first member 8 and second member 30 to be mutually connected by means of a simple operation as a result of engagement with male portion 10 provided on first member 8. This engagement mechanism might for example be a mechanism comprising a pawl-shaped female portion and a male portion shaped so as to engage with this pawl, first member 8 and second member 30 being capable of being easily locked in connected relationship as a result of the mutual engagement which is made to occur between this pawl and this region that engages with the pawl. Note that the foregoing engagement mechanism may have a structure which is other than this.

Second hollow needle member 34, which is needle-shaped and has hollow interior, is such that tip portion 36 thereof is arranged so as to be directed toward first member 8 (first hollow needle member 12), and is such that base portion 38 thereof is arranged so as to be directed toward the portion (syringe barrel connection portion 44) which makes connection with syringe barrel 6. Furthermore, tip portion 36 is supported in such state that it is inserted within second elastic member 40, described below, and base portion 38 is held in fixed fashion by syringe barrel connection portion 44. Moreover, during delivery of drug(s), first member 8 and second member 30 are mutually connected, and second hollow needle member 34 is inserted within first hollow needle member 12. This being the case, as the orientation of second hollow needle member 34 is held in fixed fashion so as to be in a prescribed direction, member 8, 30 interconnection operations (hollow needle member 12, 34 insertion operations) can be carried out easily and definitively.

Furthermore, because liquid drug delivery between drug container 2 and syringe barrel 6 is carried out by way of second hollow needle member 34, hole(s) for delivery of drug(s) are provided at least at tip portion 36 and base portion 38.

Second elastic member 40 might for example be a spherically shaped member, the material of which is silicon, thermoplastic resin, or other such substance provided with elasticity. Furthermore, second elastic member 40 is held in fixed fashion at a prescribed location within second member 30 by second fixing member 42. Here, what is meant by a prescribed location is a location such that, when first member 8 and second member 30 are mutually connected, first elastic member 18 and second elastic member 40 are made to mutually abut such that there is a prescribed force therebetween.

Second fixing member 42, as has been described, is a member for holding second elastic member 40 in fixed fashion at a prescribed location within second member 30. Second fixing member 42, which is of bowl-like shape and has hole(s) at the base portion thereof, engagement of this bowl-like region by the spherically shaped second elastic member 40 causing second elastic member 40 to be held in fixed fashion at the prescribed location.

Figure 9:
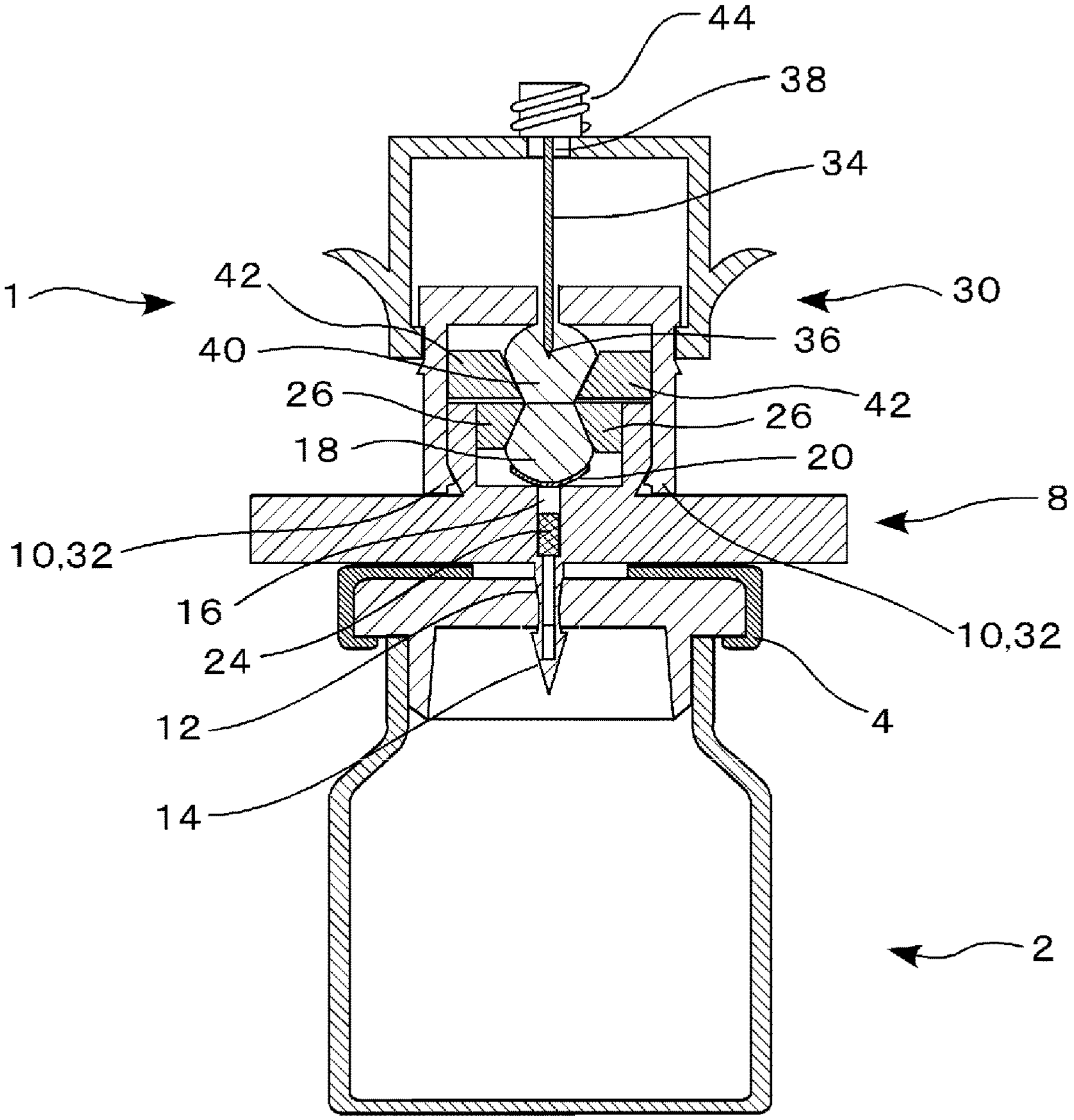
FIG. 9 Sectional view to assist in describing a way in which a first member and a second member associated with the present embodiment might be connected.
Figure 10:
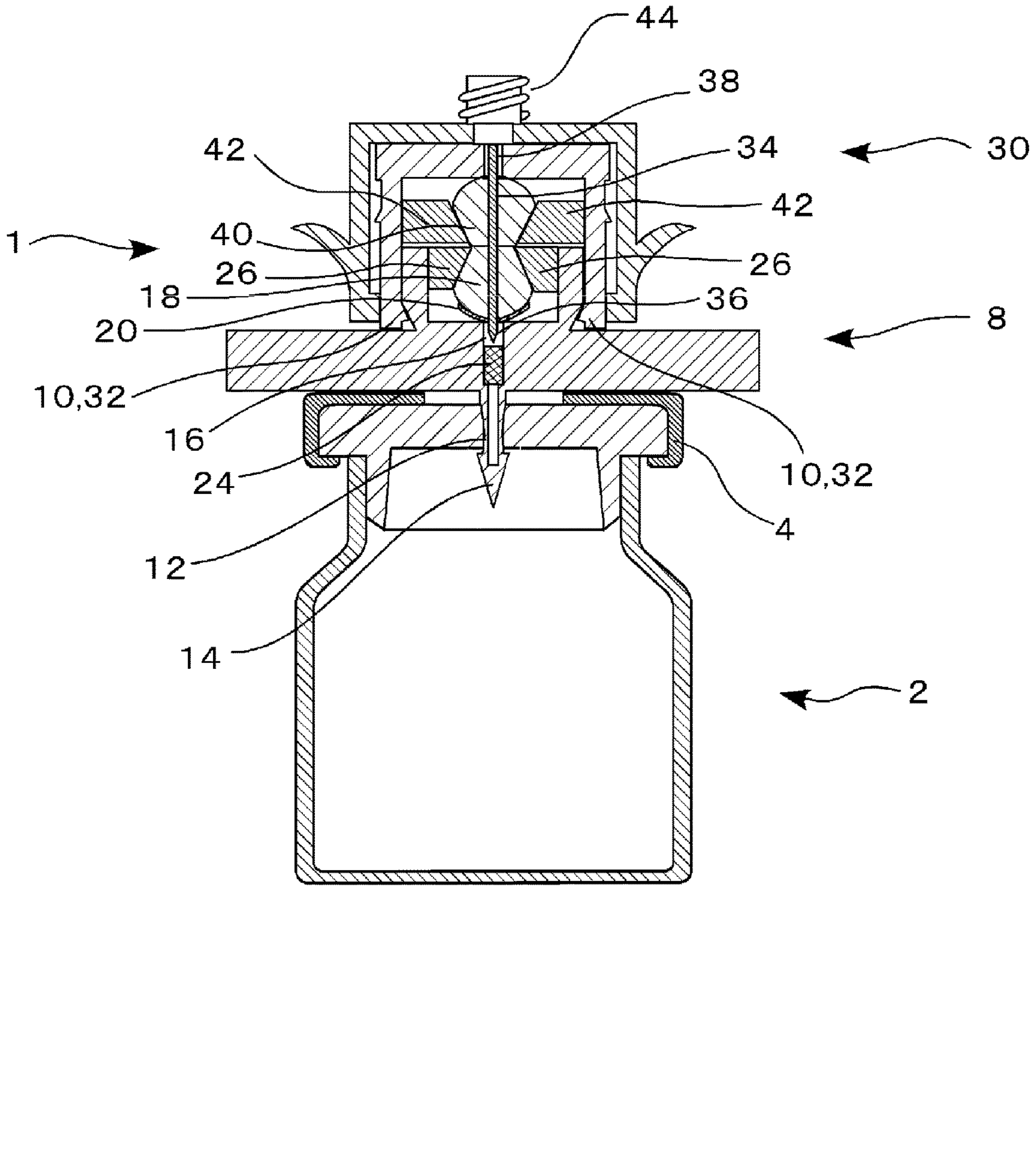
FIG. 10 Sectional view to assist in describing a way in which a first member and a second member associated with the present embodiment might be connected.

Next, FIG. 9 and FIG. 10 will be used to describe the manner in which first member 8 and second member 30 are connected. FIG. 9 and FIG. 10 are sectional views to assist in describing ways in which first member 8 and second member 30 may be connected.

As shown in FIG. 9, in a first procedure, male portion 10 and female portion 32 of an engagement mechanism for causing first member 8 and second member 30 to be mutually connected are mutually engaged, causing first member 8 and second member 30 to be mutually connected. While in this state, first elastic member 18 and second elastic member 40 mutually abut, the region where elastic members 18, 40 abut assumes a squashed state, and the region where first member 8 and second member 30 mutually connect becomes a closed system which is closed off from the exterior.

In addition, as shown in FIG. 10, in a second procedure, while maintaining the foregoing state without alteration, tip portion 36 of second hollow needle member 34, which is supported by second elastic member 40, is pressed upon and made to advance so as to penetrate the interior of second elastic member 40 and first elastic member 18, such that the interior of first hollow needle member 12 is entered from base portion 16. At such time, because there is a possibility that second hollow needle member 34 will scrape off matter from elastic members 18, 40, first filter member 20 and second filter member 24 are employed to prevent such debris 46 which may be produced by scraping from being able to pass therethrough.

In addition, tip portion 14 of first hollow needle member 12 is inserted into stopper 4 of drug container 2, such that liquid drug delivery between drug container 2 and syringe barrel 6 occurs by way of hollow needle members 12, 34.

Figure 11:
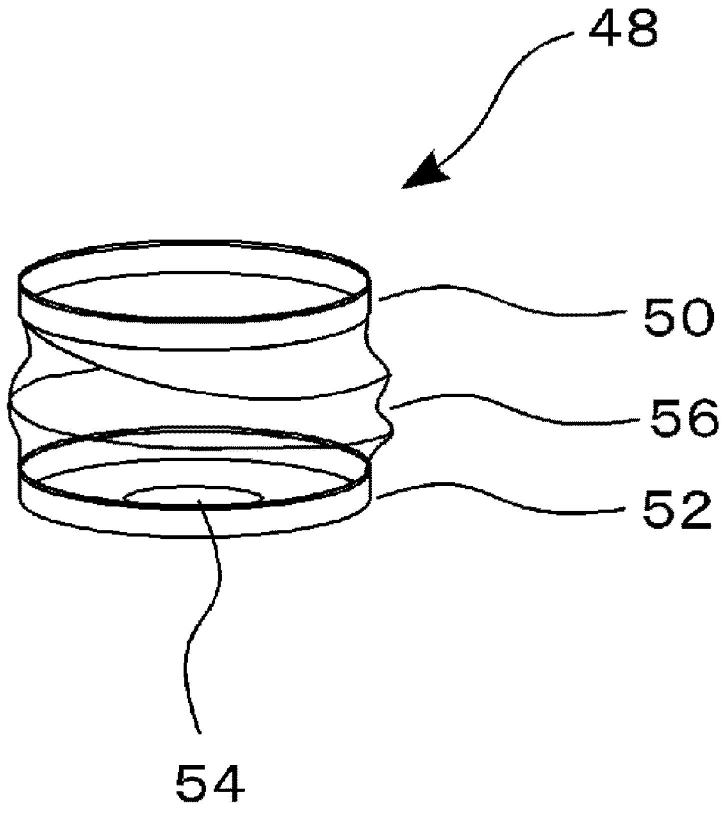
FIG. 11 Perspective view of a third member associated with the present embodiment.

Next, FIG. 11 will be used to describe the structure of third member 48. FIG. 11 is a perspective view of third member 48. As shown in FIG. 11, third member 48 has open portion(s) 50, bottom portion(s) 52, and flexible member(s) 56.

Open portion 50 is a region for allowing drug container(s) 2 to be inserted within the interior of third member 48 when drug container(s) 2 are to be placed within the interior of third member 48. Furthermore, open portion 50 is also provided with ability to squeeze on first member 8, squeezing of first member 8 by open portion 50 causing mutual connection to be made, and permitting said connected state to be maintained, between first member 8 and third member 48. In such case, due to the fact that first member 8 acts as cover for third member 48, the interior of third member 48 assumes a sealed state.

Note that an embodiment may also be adopted in which first member 8 and third member 48 are mutually connected as a result of causing drug container gripping portion 28 provided at first member 8 to be squeezed on by open portion 50. Furthermore, an embodiment of open portion 50 may, e.g., if the material employed therefor is an elastic member such as rubber or the like, be such that it is provided with a mechanism permitting adjustment of the length of its perimeter in correspondence to the size of the region on first member 8 at which connection is made.

As bottom portion 52 is a region on which drug container 2 will be placed, it is preferred that it be flat in shape for stable placement of drug container 2 thereon. Moreover, for stable placement of drug container 2 thereon, bottom portion 52 may be provided with an antislip mechanism or other such mechanism for causing drug container 2 to be held in fixed fashion.

Bottom portion 52 is provided with magnifying lens(es) 54 so as to permit observation of the interior of drug container 2 from the bottom of drug container 2 placed thereon. Even where drug container 2 has been sealed by third member 48, because bottom portion 52 is provided with magnifying lens(es) 54, it is possible to carry out inspection (operations permitting observation of the situation existing at the drug(s) at the interior of drug container 2) of drug container 2 from the exterior.

Flexible member 56 is a member for covering drug container 2 placed on bottom portion 52, being a member whose height is adjustable such that one end 58 thereof joins with the perimeter of open portion 50, and the other end 60 thereof joins with the perimeter of bottom portion 52. It is preferred that flexible member 56 be a soft material. Furthermore, because the height of flexible member 56 is adjustable, it may be bellows-like in shape. When flexible member 56 is provided with such properties, drug delivery device 1 will be able to cause drug container 2 to be maintained in a sealed state regardless of the height of drug container 2.

Flexible member 56 is a member which allows drug container 2 to be visible from the side(s) when drug container 2 is placed on bottom portion 52 and covered by flexible member 56. For this reason, it is preferred that flexible member 56 be a transparent material. Furthermore, when first member 8 and third member 48 are mutually connected, a state is assumed in which flexible member 56 covers drug container gripping portion 28.

Figure 12:
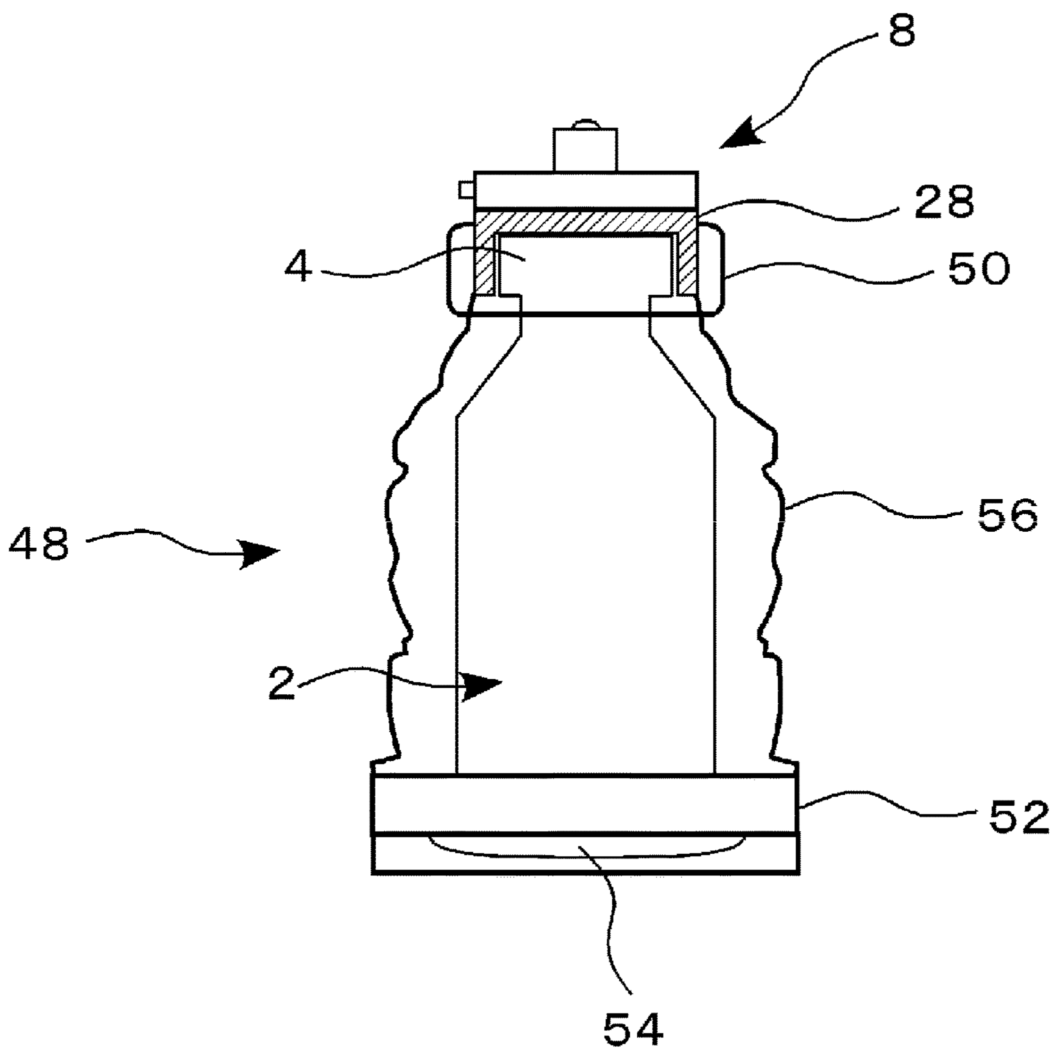
FIG. 12 Side view to assist in describing a way in which a first member and a third member associated with the present embodiment might be connected.

Next, FIG. 12 will be used to describe the manner in which connection is made between first member 8 and third member 48. FIG. 12 is a side view to assist in describing ways in which first member 8 and third member 48 may be connected.

As shown in FIG. 12, in a first procedure, drug container 2, which is connected to first member 8, is inserted within open portion 50, and the bottom of drug container 2 is made to touch bottom portion 52, to place drug container 2 on bottom portion 52.

As shown in FIG. 12, in a second procedure, open portion 50 and flexible member 56 are raised, and the height of flexible member 56 is adjusted in correspondence to the height of drug container 2. In addition, in a third procedure, open portion 50 is connected to first member 8, and drug container 2 which is present at the interior of third member 48 is made to assume a sealed state.

(Method for Using Drug Delivery Device Associated with Present Embodiment)

(1) Drug Delivery Operations

FIG. 1, FIG. 2, FIG. 4, FIG. 6, FIG. 7, FIG. 9, and FIG. 10 will be used to describe methods for using drug delivery device 1; and more specifically, methods for delivering drug(s) between drug container(s) 2 and syringe barrel(s) 6 in the context of drug delivery system(s) 100 which include drug delivery device(s) 1. Note that the present description is predicated on drug delivery where drug container 2 is a vial as shown in FIG. 1, and/or is predicated on drug delivery where drug container 2 is an infusion bag as shown in FIG. 2.

In the first procedure, when an operator causes tip portion 14 of first hollow needle member 12 provided on first member 8 shown in FIG. 4 to be inserted in stopper portion 4 of drug container 2, this causes mutual connection to be made between drug container 2 and first member 8.

In the second procedure, when as shown in FIG. 6 and FIG. 7 an operator adjusts the size of drug container gripping portion 28 so that it corresponds to the magnitude of the diameter of the opening in stopper portion 4 of drug container 2, and causes stopper portion 4 (and/or the nose portion) to be squeezed on from both the left and right sides thereof, and/or from all four sides thereof, this causes the mutually connected relationship between drug container 2 and first member 8 to be made fixed.

In a third procedure, when an operator causes male portion 10 and female portion 32 of an engagement mechanism to be mutually engaged as shown in FIG. 9, this causes first member 8 and second member 30 to be mutually connected. While in this state, first elastic member 18 and second elastic member 40 mutually abut, the region where elastic members 18, 40 abut assumes a squashed state, and the region where first member 8 and second member 30 mutually connect becomes a closed system which is closed off from the exterior.

In a fourth procedure, as shown in FIG. 10, while maintaining without alteration the state reached at the conclusion of the third procedure, an operator causes tip portion 36 of second hollow needle member 34, which is supported by second elastic member 40, to be pressed upon and made to advance so as to penetrate the interior of second elastic member 40 and first elastic member 18. Moreover, the operator causes second hollow needle member 34 to be inserted within the interior of first hollow needle member 12 from base portion 16. At such time, because there is a possibility that second hollow needle member 34 will scrape off matter from elastic members 18, 40, first filter member 20 and second filter member 24 are employed to prevent such debris 46 which may be produced by scraping from being able to pass therethrough.

In a fifth procedure, as shown in FIG. 1 and/or FIG. 2, an operator causes syringe barrel 6 to be connected to syringe barrel connection portion 44 provided on second member 30.

In a sixth procedure, an operator causes drug(s) to be delivered from syringe barrel 6 to drug container 2, and/or from drug container 2 to syringe barrel 6. At such time, the operator carries out delivery of drug(s) by turning drug container 2 upside-down or by appropriately actuating syringe barrel 6.

(2) Drug Container Sealing Operations

FIG. 1, FIG. 2, and FIG. 10 through FIG. 12 will be used to describe methods for using drug delivery device 1; and more specifically, methods for causing drug container(s) 2 to assume sealed state(s) shielded from the exterior in the context of drug delivery system(s) 100 which include drug delivery device(s) 1. Note that the present description is predicated on drug delivery where drug container 2 is a vial as shown in FIG. 1, and/or is predicated on drug delivery where drug container 2 is an infusion bag as shown in FIG. 2.

In the first procedure, an operator causes drug container 2, which is connected to first member 8 shown in FIG. 10, to be inserted within open portion 50 shown in FIG. 11, such that the bottom of drug container 2 is inserted therewithin first, and the bottom of drug container 2 is made to touch bottom portion 52, to place drug container 2 on bottom portion 52.

In a second procedure, an operator raises open portion 50 and flexible member 56 in correspondence to the height of drug container 2 placed on bottom portion 52.

In a third procedure, as shown in FIG. 12, an operator closes first member 8 with open portion 50, and causes first member 8 and third member 48 to be mutually connected. These operations cause drug container 2 to assume a sealed state within the interior of third member 48.

After execution of the third procedure, when it is desired that the interior of drug container 2 which is sealed by third member 48 be checked, e.g., to inspect drug container 2, an operator can check the interior of drug container 2 by way of magnifying lens 54 provided at bottom portion 52.

(Wrapup)

A drug delivery device 1 which is disclosed permits delivery of drug(s) between syringe barrel(s) 6 and drug container(s) 2 while preventing exposure to hazardous drug(s) adhering to drug container(s) 2 by enveloping the entire container(s) at the drug container(s) 2 employed for delivery of drug(s).

A drug delivery device 1 which is disclosed permits prevention of exposure to hazardous drug(s) adhering to drug container(s) 2 by varying height(s) of sealing equipment 48 in correspondence to size(s) of drug container(s) 2 employed for delivery of drug(s), and by forming sealed state(s) at drug container(s) 2 without dependence on size(s) of drug container(s) 2.

A drug delivery device 1 which is disclosed permits, for drug container(s) 2 in sealed state(s), observation of the situation existing within drug container(s) 2, and in particular of the situation existing at drug(s) within drug container(s) 2, while sealed state(s) are maintained, by checking interior(s) of drug container(s) 2 from direction(s) of bottom(s) by way of magnifying lens(es).

While embodiments of the present invention have been described in detail above, the present invention is not limited to any such particular embodiment, variation and/or alteration being possible within the range of the gist of the present invention as recited at the claims.

EXPLANATION OF REFERENCE NUMERALS

1 Drug delivery device
2 Drug container
4 Drug container stopper
6 Syringe barrel
8 First member
10 Engagement mechanism male portion
12 First hollow needle member
14 First hollow needle member tip portion
16 First hollow needle member base portion
18 First elastic member
20 First filter member
22 Screen-like member

24 Second filter member
26 First fixing member
28 Drug container gripping portion
30 Second member
32 Engagement mechanism female portion
34 Second hollow needle member
36 Second hollow needle member tip portion
38 Second hollow needle member base portion
40 Second elastic member
42 Second fixing member
44 Syringe barrel connection portion
46 Unwanted material
48 Third member
50 Open portion
52 Bottom portion
54 Magnifying lens
56 Flexible member
58 One end of flexible member
60 Other end of flexible member
100 Drug delivery system

The invention claimed is:

1. A drug delivery device that has a first member which is connected to a stopper side of a drug delivery device, a second member which is connected at one end thereof to said first member and which is connected at another end thereof to a syringe barrel, and a third member which is connected to the first member and which is for covering the drug container in a sealed state; and that carries out delivery of a drug between the drug container and the syringe barrel, the drug delivery device characterized in that:

the first member has
- a first hollow needle member having a tip portion arranged so as to be directed toward the stopper side of the drug delivery device, and having a base portion arranged so as to be directed toward the second member, the base portion and the tip portion each being provided with a hole for delivery of the drug; and
- a drug container gripping portion that allows a size of a region at which connection occurs to be varied in correspondence to a magnitude of an outside diameter at the drug container stopper portion, and that squeezes on and holds the drug container stopper;

the second member has
- a second hollow needle member having a tip portion arranged so as to be directed toward the first member, and having a base portion arranged so as to be directed toward the syringe barrel, the base portion and the tip portion each being provided with a hole for delivery of the drug; and the third member has
- an open portion;
- a bottom portion permitting stable placement of the drug container thereon; and
- a flexible member that is connected at one end thereof to the open portion and is connected at another end thereof to the bottom portion, that allows the drug container when placed on the bottom portion to be visible from an exterior side, that is of adjustable height, and that covers the drug container;

wherein mounting the open portion on the first member while in a state in which the flexible member covers the drug container gripping portion causes the first member and the third member to be mutually connected while an interior of the third member is in a sealed state;

wherein, when the first member and the second member are mutually connected, the second hollow needle member is inserted within the first hollow needle member which is inserted in the stopper of the drug container; and wherein, after the drug container gripping portion has caused the connected relationship between the drug container and the first member to become fixed, delivery of the drug between the drug container and the syringe barrel is carried out by way of the first hollow needle member and the second hollow needle member which is inserted within said first hollow needle member.

2. A drug delivery device according to claim 1 characterized in that the bottom portion has a magnifying lens capable of magnifying and making visible a drug container bottom placed on the bottom portion.

3. A drug delivery device according to claim 1 characterized in that a size of the open portion is adjustable.

* * * * *